(12) United States Patent
Mittelsteadt et al.

(10) Patent No.: US 7,947,405 B2
(45) Date of Patent: May 24, 2011

(54) SOLID POLYMER ELECTROLYTE COMPOSITE MEMBRANE COMPRISING POROUS CERAMIC SUPPORT

(75) Inventors: Cortney K. Mittelsteadt, Wayland, MA (US); Anthony B. LaConti, Lynnfield, MA (US)

(73) Assignee: Giner Electrochemical Systems, LLC, Newton, MA (US)

( * ) Notice: Subject to any disclaimer, the term of this patent is extended or adjusted under 35 U.S.C. 154(b) by 1474 days.

(21) Appl. No.: 11/239,647

(22) Filed: Sep. 29, 2005

(65) Prior Publication Data

US 2006/0183011 A1 Aug. 17, 2006

Related U.S. Application Data

(60) Provisional application No. 60/614,143, filed on Sep. 29, 2004.

(51) Int. Cl.
*H01M 8/10* (2006.01)
*B05D 5/12* (2006.01)
*C25D 1/00* (2006.01)
*C08G 75/24* (2006.01)

(52) U.S. Cl. ........ 429/465; 429/479; 429/486; 427/115; 205/538; 528/391

(58) Field of Classification Search .................. None
See application file for complete search history.

(56) References Cited

U.S. PATENT DOCUMENTS

| | | | |
|---|---|---|---|
| 3,282,875 A | 11/1966 | Connolly et al. |
| 3,972,727 A | 8/1976 | Cohn |
| 4,215,183 A | 7/1980 | MacLeod |
| 4,470,889 A | 9/1984 | Ezzell et al. |
| 4,478,695 A | 10/1984 | Ezzell et al. |
| 4,849,311 A | 7/1989 | Itoh et al. |
| 5,569,855 A | 10/1996 | Schomburg et al. |
| 6,350,389 B1 | 2/2002 | Fujishima et al. |

(Continued)

FOREIGN PATENT DOCUMENTS

JP 1158051 A 6/1989

(Continued)

OTHER PUBLICATIONS

Weidner et al., "Engineering a Membrane Electrode Assembly," The Electrochemical Society Interface, 12(4):40-43 (Winter 2003).

*Primary Examiner* — Dah-Wei Yuan
*Assistant Examiner* — Angela J. Martin
(74) *Attorney, Agent, or Firm* — Kriegsman & Kriegsman (57) ABSTRACT

A solid polymer electrolyte composite membrane and method of manufacturing the same. The composite membrane comprises a porous ceramic support having a top surface and a bottom surface. The porous ceramic support may be formed by laser micromachining a ceramic sheet or may be formed by electrochemically oxidizing a sheet of the base metal. A solid polymer electrolyte fills the pores of the ceramic support and preferably also covers the top and bottom surfaces of the support. Application of the solid polymer electrolyte to the porous support may take place by applying a dispersion to the support followed by a drying off of the solvent, by hot extrusion of the solid polymer electrolyte (or by hot extrusion of a precursor of the solid polymer electrolyte followed by in-situ conversion of the precursor to the solid polymer electrolyte) or by in-situ polymerization of a corresponding monomer of the solid polymer electrolyte.

26 Claims, 4 Drawing Sheets

U.S. PATENT DOCUMENTS

| | | |
|---|---|---|
| 6,492,431 B1 | 12/2002 | Cisar |
| 6,500,319 B2 | 12/2002 | LaConti et al. |
| 6,586,133 B1 | 7/2003 | Teeters et al. |
| 6,635,384 B2 | 10/2003 | Bahar et al. |
| 6,793,711 B1 | 9/2004 | Sammells |
| 2002/0182482 A1 | 12/2002 | Hockaday et al. |
| 2003/0138656 A1 | 7/2003 | Sparks |
| 2004/0033403 A1* | 2/2004 | Mardilovich et al. ........... 429/30 |
| 2004/0126638 A1 | 7/2004 | Chen et al. |
| 2005/0026030 A1 | 2/2005 | Mardilovich |
| 2005/0074651 A1 | 4/2005 | Kidai et al. |
| 2005/0095486 A1 | 5/2005 | Hamamoto et al. |
| 2005/0260485 A1* | 11/2005 | Sopchak et al. ................ 429/46 |
| 2005/0263452 A1 | 12/2005 | Jacobson |
| 2006/0065521 A1 | 3/2006 | Liu et al. |
| 2006/0065522 A1 | 3/2006 | Liu et al. |

FOREIGN PATENT DOCUMENTS

| | | |
|---|---|---|
| JP | 2230662 A | 9/1990 |
| JP | 2291607 A | 12/1990 |
| WO | WO 02/081097 A1 | 10/2002 |
| WO | WO 2004/045750 A1 | 6/2004 |

* cited by examiner

SOLID POLYMER ELECTROLYTE COMPOSITE MEMBRANE COMPRISING POROUS CERAMIC SUPPORT

CROSS-REFERENCE TO RELATED APPLICATIONS

The present application claims the benefit under 35 U.S.C. 119(e) of U.S. Provisional Patent Application Ser. No. 60/614,143, filed Sep. 29, 2004, the disclosure of which is incorporated herein by reference.

BACKGROUND OF THE INVENTION

The present invention relates generally to solid polymer electrolyte membranes of the type suitable for use in electrochemical devices and relates more particularly to a novel such membrane.

Electrochemical devices of the type comprising a solid polymer electrolyte membrane (PEM) sandwiched between a pair of electrodes are well-known, such electrochemical devices finding applications as, for example, fuel cells, electrolyzers, sensors, gas concentrators, gas compressors, supercapacitors, ultracapacitors and industrial electrochemical process units.

A common type of solid polymer electrolyte membrane consists of a homogeneous perfluorosulfonic acid (PFSA) polymer, said PFSA polymer being formed by the copolymerization of tetrafluoroethylene and perfluorovinylether sulfonic acid. See e.g., U.S. Pat. No. 3,282,875, inventors Connolly et al., issued Nov. 1, 1966; U.S. Pat. No. 4,470,889, inventors Ezzell et al., issued Sep. 11, 1984; U.S. Pat. No. 4,478,695, inventors Ezzell et al., issued Oct. 23, 1984; U.S. Pat. No. 6,492,431, inventor Cisar, issued Dec. 10, 2002, all of which are incorporated herein by reference. A commercial embodiment of a perfluorosulfonic acid polymer PEM is available from DuPont (Wilmington, Del.) as NAFION® PFSA polymer.

Although PFSA PEMs function in a generally satisfactory manner in electrochemical devices, there nonetheless remains room for improvement in certain properties of PFSA PEMs. For example, one common difficulty associated with PFSA PEMs is a lack of mechanical strength, resulting in a tendency for the PFSA PEMs to tear, especially when being handled (such as during assembly of an electrochemical cell) or in stressed areas where compression is applied thereto (such as in peripheral areas of PEMs sealed under pressure to other electrochemical cell components). Such a lack of mechanical strength also often leads to electrical shorting, which results in premature failures during cell operation as the typical porous electrodes in contact with the PEM have a tendency to penetrate the softened PEM. This problem of shorting is even greater when the membrane is made thin (e.g., less than 25 microns) in order to decrease membrane resistance.

Because the tendency to tear and to short is greatest when the PFSA PEMs are wet (especially at elevated temperatures) and because the PFSA PEMs must be wet in order to function properly, one approach to this problem has been to assemble electrochemical cells with dry PEMs and then to subject the PEMs to a humidification process. This approach, however, has its own shortcomings. One such shortcoming is that the dry assembly requires special moisture-free facilities, such as a "dry room." Another such shortcoming is that the humidification process is time-consuming. Still another such shortcoming is that the humidification process typically results in the PEM swelling in a non-uniform manner, thereby creating stress in some areas of the PEM, as well as in other components of the cell that are in contact with the PEM, and introducing irregularities in the contact pressure applied over the entire active surface area of the PEM. (When the contact pressure is not uniform over the entire active surface area of the PEM, the performance of the electrochemical cell is adversely affected.) As can readily be appreciated, such irregularities are amplified where humidification is applied to a plurality of PEM-containing fuel cells arranged in a stack.

Moreover, if the PEM is subjected to variable conditions of humidity (e.g., alternating wet and dry intervals during periods of use and non-use, respectively), the membrane will undergo additional dimensional changes as it swells when wet and shrinks when dry. Such dimensional changes cause further stress to the PEM and to the other cell components, all of which are tightly packed together. If sufficiently great, such stress results in damage to the PEM and/or to the cell components in contact therewith. Pinholes/microcracks have a tendency to form along the cell or flow-field edges where one side of the membrane is heavily compressed by the fixture while the other side can still partially swell.

One approach that has been taken to address the aforementioned problem of low mechanical strength of PFSA PEMs has been to cross-link the membrane polymer. Such cross-linking reduces the swelling of the membrane when wet which, in turn, reduces the deterioration of the mechanical strength of the membrane when wet. Unfortunately, however, such cross-linking tends to make the membrane undesirably brittle under dry conditions.

Another approach to this problem is disclosed in U.S. Pat. No. 6,635,384, inventors Bahar et al., which issued Oct. 21, 2003, and which is incorporated herein by reference. In the aforementioned '384 patent, there is described a composite membrane that comprises a microporous sheet, said microporous sheet preferably being an expanded polytetrafluoroethylene (ePTFE) membrane, said ePTFE membrane preferably being formed by stretching a sheet of polytetrafluoroethylene (PTFE) until pores are formed therein. The structure defining the pores of the microporous sheet is then at least partially covered with a functional material selected from (i) inorganic particulate; (ii) metal; and (iii) an organic polymer. In addition, the pores of the sheet are then at least partially filled with polymer electrolyte selected from (i) polymer compositions that contain metal salts; (ii) polymeric gels that contain electrolyte; and (iii) ion exchange resins, such as PFSA.

One disadvantage that has been noted by the present inventors regarding the foregoing composite membrane is that the pores of the expanded polytetrafluoroethylene (ePTFE) sheet tend to follow a tortuous pathway between opposing surfaces of the ePTFE sheet, as opposed to following a direct or straight pathway between opposing surfaces. As a result of these tortuous pathways, protons conducted through the pores (by means of the polymer electrolyte that is disposed within the pores) have to travel considerably longer pathways through the membrane than merely the thickness of the membrane. Such longer pathways result in a reduction in the conductivity of the membrane and an increase in the resistivity of the membrane.

Another disadvantage that has been noted by the present inventors regarding the foregoing composite membrane is that a microporous sheet of ePTFE possesses only slightly better mechanical strength than a PFSA PEM. Consequently, the foregoing composite membrane is not significantly stronger than a PFSA PEM and is subject to the same types of shortcomings discussed above in connection with PFSA PEMs.

Still another disadvantage that has been noted by the present inventors regarding the foregoing composite membrane is that the stretching process that is used to expand the PTFE sheet to create the desired pores tends to result in a fairly uniform yet random distribution of pores throughout the sheet and cannot be tailored to control the positioning or concentration of pores in particular regions of the sheet. This is unfortunate because certain regions of the membrane, such as the membrane active area edges/corners or the membrane contact area with the current collector, are typically subjected to greater stresses than other regions. Consequently, pores in these regions of high stress undesirably diminish membrane strength in those regions where membrane strength is needed most.

SUMMARY OF THE INVENTION

It is an object of the present invention to provide a novel solid polymer electrolyte membrane of the type that is suitable for use in electrochemical devices, such as, but not limited to, fuel cells, electrolyzers, sensors, gas concentrators, gas compressors, supercapacitors, ultracapacitors and industrial electrochemical process units.

It is another object of the present invention to provide a solid polymer electrolyte membrane of the type described above that overcomes at least some of the drawbacks discussed above in connection with existing solid polymer electrolyte membranes.

Therefore, according to one aspect of the invention, there is provided a solid polymer electrolyte composite membrane, said solid polymer electrolyte composite membrane comprising (a) a ceramic support, said ceramic support having opposing top and bottom surfaces and a plurality of pores extending from said top surface to said bottom surface; and (b) a first solid polymer electrolyte at least partially filling at least some of said pores.

In a preferred embodiment, the ceramic support contains or is made of at least one of silica, quartz, glass, boron carbonate, silicon carbide, alumina, titania, silica tungstate, sintered valve metal oxides (e.g., tantalum or niobium oxide) and non-conductive diamond or diamond-like coatings, the support having a thickness of about 1 µm to 50 µm. A plurality of cylindrical pores are formed in the support by laser micromachining. The pores have a diameter of about 1 µm to 200 µm and are arranged in a defined pattern, such as in a uniform hexangular pattern or in a pattern in which fewer pores are located in areas of higher membrane stress and more pores are located in areas of lower membrane stress. A solid polymer electrolyte, such as PFSA polymer, fills the pores. This may be effected, for example, by filling the pores with a solution/dispersion of the solid polymer electrolyte and then drying off the solvent, by filling the pores with a precursor of the solid polymer electrolyte and then converting said precursor to said solid polymer electrolyte by base hydrolysis, or by filling the pores with a monomer of the solid polymer electrolyte and then polymerizing the monomer in-situ. Additional solid polymer electrolyte, which may be the same as or different than that filling the pores, may be applied to one or both of the top and bottom surfaces of the ceramic support.

In another preferred embodiment, a porous ceramic support is prepared by the controlled electrochemical oxidation of a sheet of the base metal. The pores of such a support may have a diameter of about 0.01 micron to 100 microns and may be arranged in a honeycomb pattern. Where the pores have a diameter less than about 0.1 micron, the pores are preferably not filled using a solution/dispersion of the solid polymer electrolyte, but rather, are preferably filled using the techniques identified above involving base hydrolysis of a precursor or by in-situ polymerization.

The present invention is also directed at methods of preparing a solid polymer electrolyte composite membrane. According to one aspect, said method comprises the steps of (a) providing a ceramic support, said ceramic support having a top surface and a bottom surface; (b) lasing at least one pore in said ceramic support, said at least one pore extending transversely from said top surface to said bottom surface; and (c) filling at least one of said at least one pore with a first solid polymer electrolyte.

According to another aspect, said method comprises the steps of (a) providing a metal sheet; (b) electrochemically oxidizing said metal sheet to form a ceramic support having a top surface and a bottom surface, said ceramic support having at least one pore extending transversely from said top surface to said bottom surface; and (c) filling at least one of said at least one pore with a first solid polymer electrolyte.

The present invention is further directed at a method of preparing a perfluorosulfonic acid polymer, said method comprising the steps of (a) providing a sulfonyl fluoride precursor of said perfluorosulfonic acid polymer; and (b) adding a weak base to said sulfonyl fluoride precursor to convert said sulfonyl fluoride precursor to said perfluorosulfonic acid polymer.

The present invention is also directed to membrane electrode assemblies incorporating the above-described composite membranes and to electrochemical devices incorporating the above-described composite membranes, such electrochemical devices including, but not being limited to, fuel cells, electrolyzers, gas concentrators, gas compressors, sensors, supercapacitors, ultracapacitors, and industrial electrochemical process units.

For purposes of the present specification and claims, it is to be understood that certain relational terms used herein, such as "above," "below," "top," "bottom," "over," "under," "in front of," or "behind," when used to denote the relative positions of two or more components of an electrochemical device are used to denote such relative positions in a particular orientation and that, in a different orientation, the relationship of said components may be reversed or otherwise altered.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1:
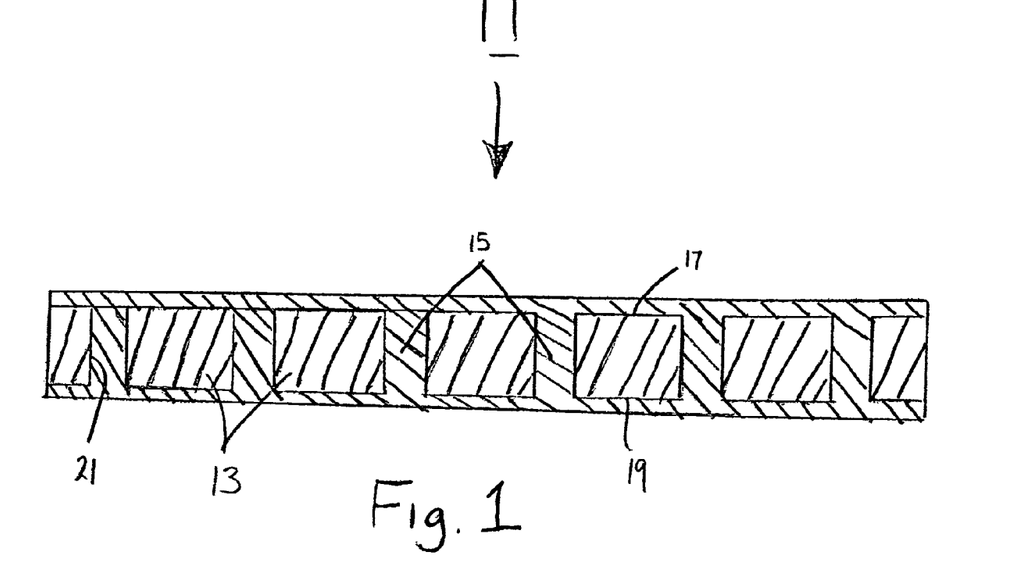
FIG. 1 is a schematic section view of a first embodiment of a solid polymer electrolyte composite membrane constructed according to the teachings of the present invention.

Referring now to FIG. 1, there is shown a schematic section view of a first embodiment of a solid polymer electrolyte composite membrane constructed according to the teachings of the present invention, said solid polymer electrolyte composite membrane being represented generally by reference numeral 11.

Composite membrane 11 comprises a non-electrically-conductive support 13 and a solid polymer electrolyte 15, support 13 being impregnated with solid polymer electrolyte 15.

Figure 2A:
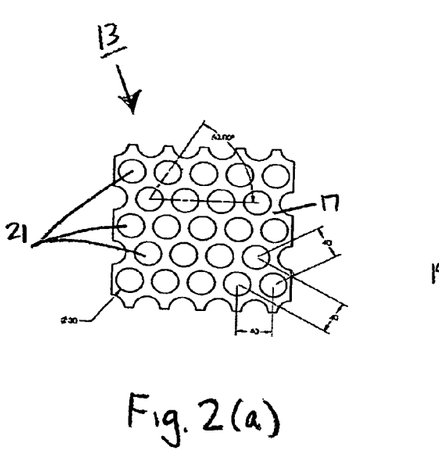
FIGS. 2(a) and 2(b) are top and perspective views, respectively, of the non-electrically-conductive support shown in FIG. 1.
Figure 2B:
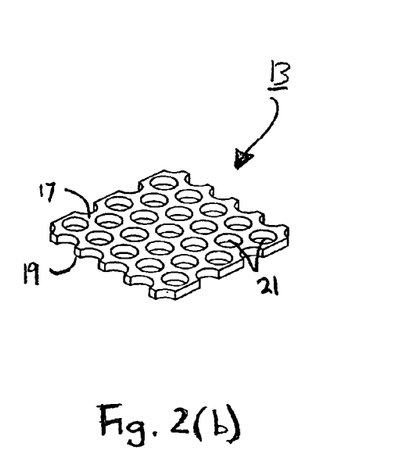

Referring now to FIGS. 2(a) and 2(b), support 13 can be seen to be a generally sheet-like, unitary structure, preferably of high mechanical strength, having a top surface 17 and a bottom surface 19. The thickness of support 13 may vary, depending upon the type of use to which membrane 11 is put and the types of pressures typically encountered by support 13 in such a use. For example, where membrane 11 is used in an electrolyzer, support 13 preferably has a thickness suitable for withstanding pressures of 2000-5000 psi. For most applications, support 13 has a thickness of about 1 μm to 50 μm, preferably about 7.5 μm to 15 μm.

As noted above, support 13 is preferably a rigid member; in addition, support 13 is preferably chemically resistant to acid and water hydrolysis at elevated temperatures. Materials suitable for use as support 13 include, but are not limited to, silica, quartz, glass, boron carbonate, silicon carbide, alumina, titania, silica tungstate, sintered valve metal oxides (e.g., tantalum or niobium oxide) and non conductive diamond or diamond-like coatings. A comparison of the mechanical strength of some of the above-listed ceramics to conventional PEM materials is provided below in TABLE I.

TABLE I

| Material, condition | Young's Modulus (Mpa) |
|---|---|
| NAFION ® 112 PFSA membrane, dry 20° C. | 300 |
| NAFION ® 112 PFSA membrane, wet 80° C. | 70 |
| Polytetrafluoroethylene (PTFE) | 400 |
| SiO$_2$ (VYCOR) | 66,000 |
| Al$_2$O$_3$ | 350,000 |
| SiC | 470,000 |

As can be seen, the ceramic materials (SiO$_2$, Al$_2$O$_3$ and SiC) are orders of magnitude stronger than PFSA and PTFE.

A plurality of pores 21, preferably cylindrical in shape, extend in a direct, i.e. straight-line, fashion from top surface 17 to bottom surface 19 of support 13. It should be stressed that the base shape of the pore can be chosen from any two-dimensional geometric shape distributed in either regular or irregular fashion. As will be discussed further below, pores 21 are made by laser micromachining. Each pore preferably has 21 a diameter of about 1 μm to 200 μm, with pores 21 constituting about 20% to 95%, more preferably about 40% to 70%, of support 13.

The conductance of a membrane including such a porous support can be easily estimated as:

$$\frac{1}{G} = \frac{T_s}{\sigma * A * X} + \frac{(T - T_s)}{\sigma * A}$$

where G is the ionic conductance of the composite membrane, σ is the ionic conductivity of the solid polymer electrolyte, A is the geometric area of the composite membrane, X is the percentage of pores in the support, T is the thickness of the composite membrane and $T_s$ is the thickness of the support.

As can be seen from the above equation, the conductance of the composite membrane is inversely proportional to the percentage of pores in the support. Thus, a support with 50% pores results in a composite membrane with conductance equivalent to a homogenous membrane twice as thick. To maximize the conductance of the supported membrane without a sacrifice in mechanical properties, a support with 50% pores may be fabricated.

Figure 3:
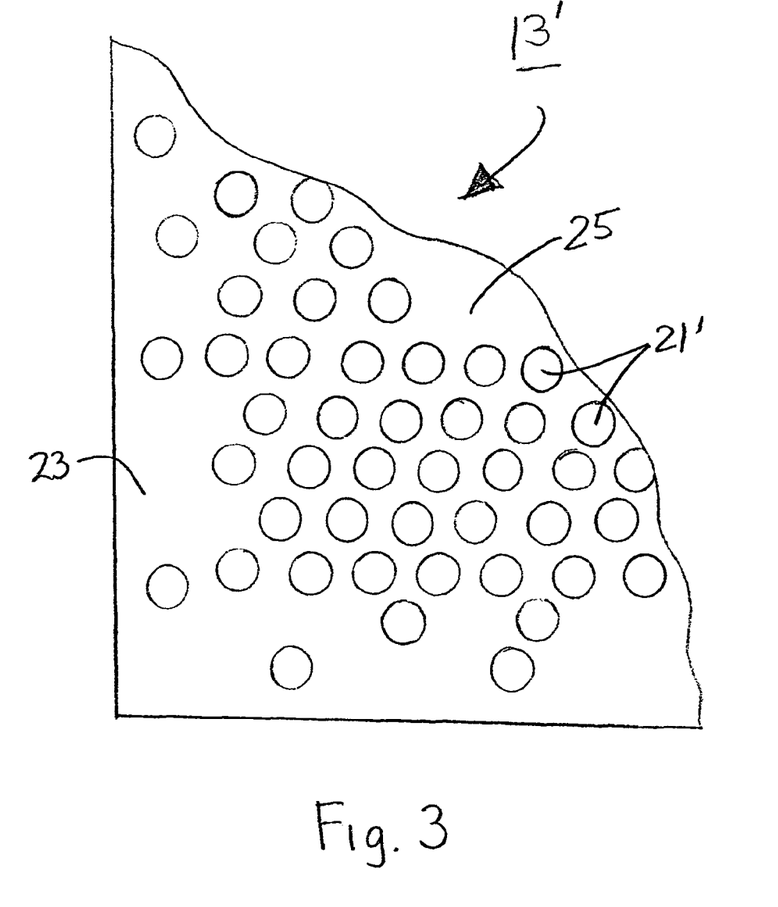
FIG. 3 is a fragmentary top view of a non-electrically-conductive support that may be used as an alternative to the non-electrically-conductive support of FIGS. 2(a) and 2(b)

In the present embodiment, pores 21 are arranged in a uniform hexagonal pattern over the entirety of support 13, such pores 21 having, for example, a diameter of about 25 μm and a center-to-center spacing of about 40 μm. It is to be understood, however, that the present invention is not limited to the above-described pattern of pores and may encompass a variety of different patterns of pores. For example, as can be seen in FIG. 3, there is shown a fragmentary top view of a support 13' having a plurality of pores 21' that are arranged so that a lesser concentration of pores 21' may be found in areas of higher membrane stress (e.g., at the membrane edge 23 or in local "hot spots" 25) and a greater concentration of pores 21' may be found elsewhere.

Figure 4:
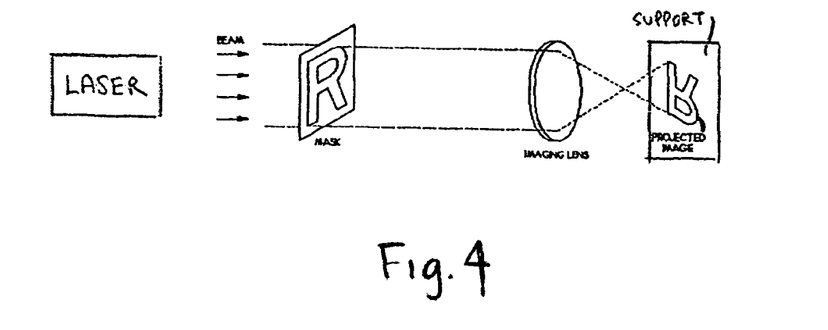
FIG. 4 is a schematic depiction of the laser micromachining technique of near-field imaging.

Pores 21 (and 21') are made by lasing support 13 with suitable laser light. Although either gas lasers or solid state lasers may be used to create pores 21, gas lasers are preferred. Within the class of gas lasers, excimer lasers are preferred over CO$_2$ lasers. This is because excimer lasers produce laser light having a much shorter wavelength than that produced by CO$_2$ lasers (~0.3 μm for an excimer laser vs. ~10 μm for a CO$_2$ laser). Consequently, because of their shorter wavelengths, excimer lasers directly excite the covalent bonds of the support and decompose the support without creating as extreme high-temperature conditions as is the case with CO$_2$ lasers. Additionally, due to their shorter wavelengths, excimer lasers can create significantly smaller pores than can CO$_2$ lasers.

Where a CO$_2$ laser is used to micromachine pores into the support, the whole laser beam is focused onto an area of the support until the irradiated area is ablated. Where an excimer laser is used, the relatively uniform beam intensity produced thereby provides an alternative approach to pore formation: near-field imaging. In near-field imaging, which is schematically depicted in FIG. 4, a mask having a pattern is placed in the path of the beam emitted by the excimer laser. The light transmitted through the pattern of the mask is then focused by an imaging lens onto the support, resulting in the mask pattern being projected onto the support, with a corresponding pattern of pores being formed in the support. As can readily be appreciated, near-field imaging enables various alternative patterns to be projected onto the support simply by using differently patterned masks.

Referring back to FIG. 1, solid polymer electrolyte 15 can be seen to fill pores 21 and to cover thinly top surface 17 and bottom surface 19 of support 13. Examples of suitable materials for use as solid polymer electrolyte 15 include (i) polymer compositions that contain metal salts; (ii) polymeric gels that contain electrolytes; and (iii) ion exchange resins. In general, if proton conductivity is required, a carboxylated, sulfonated or phosphorylated polymer is preferably used as solid polymer electrolyte 15. If hydroxyl ions are needed, a polymer containing amino, imimo, ammonium, sulfonium, and phosphonium groups is preferably used as solid polymer electrolyte 15. To enhance the ionic conductivity of membrane 11, inorganic ionically-conductive materials, such as metal oxide (e.g., $TiO_2$), silicon oxide, metal phosphates (e.g., zirconium phosphate) or heteropolyacids, may be impregnated into the solid polymer electrolyte 15.

A preferred material for use as solid polymer electrolyte 15 is a perfluorosulfonic acid (PFSA) membrane, such as is commercially available from DuPont (Wilmington, Del.) as NAFION® PFSA polymer. Of the aforementioned NAFION® PFSA polymers, particularly preferred are those having an equivalent weight of 200 to 2000, even more preferably those having an equivalent weight of 500 to 1200, the optimal equivalent weight depending on the use to which membrane 11 is applied.

Figure 5:
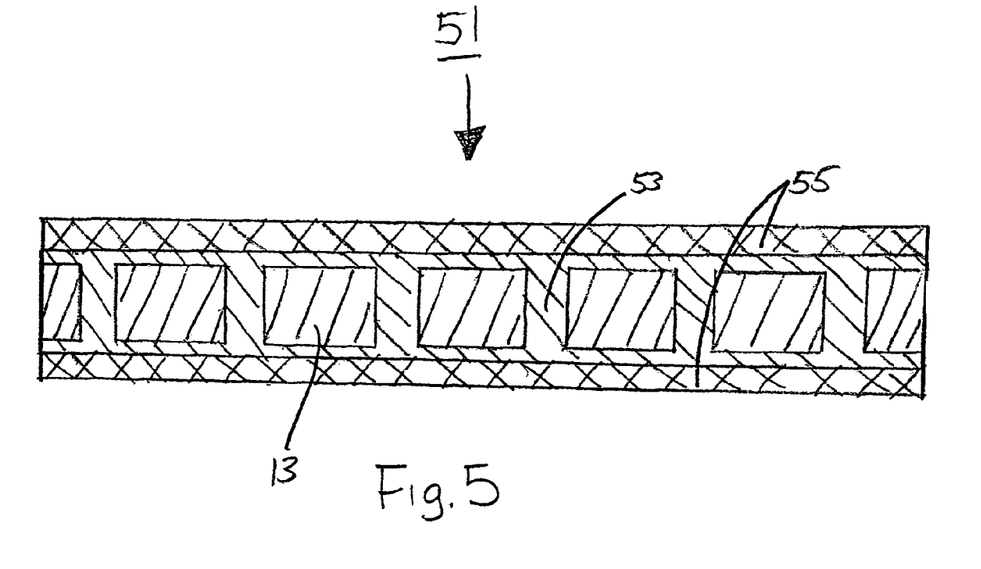
FIG. 5 is a schematic section view of a second embodiment of a solid polymer electrolyte composite membrane constructed according to the teachings of the present invention.

Various techniques may be used to couple solid polymer electrolyte 15 to support 13. One such technique involves providing the solid polymer electrolyte in the form of a solution/dispersion (e.g., NAFION® 1100 in water or isopropanol) and then coating support 13 with said solution/dispersion. Examples of suitable coating techniques include gravure coating, immersion (dip) coating, metering rod (Meyer bar) coating, slot die coating, rotary screen and air knife coating. The optimal coating technique for any particular case will depend on factors, such as instrument complexity, thickness accuracy, operation efficiency, initial investment, and the like. After the solution/dispersion is coated onto the support, the coated support is heated at about 50° C. to 100° C., preferably 80° C., for about 5 minutes to evaporate the solvent. If desired, one or more additional coatings may thereafter be applied. Said one or more additional coatings either may be of the same solution/dispersion previously applied in order to build up the thickness of the solid polymer electrolyte or may be different from the initial solution/dispersion in order to obtain a composite membrane with a multilayer electrolyte structure having desired properties. (An example of a composite membrane possessing such a multilayer structure is shown in FIG. 5, said composite membrane 51 comprising a support 13, a first solid polymer electrolyte 53 and a second polymer electrolyte 55.) After coating and drying each applied layer or after coating and drying all applied layers, the layer or layers are preferably cured by heating at a temperature greater than the glass transition temperature of the ionomer (e.g., 100° C. to 400° C., preferably 160° C. for 15 minutes). Such curing, which serves to sinter or anneal the ionomer, further enhances the mechanical properties of the membrane.

If desired, mask coating technology may be used to create a composite membrane wherein the solid polymer electrolyte is confined to certain patches or regions.

As an alternative to coating, the solid polymer electrolyte may be applied by spraying the polymer electrolyte solution/dispersion onto support 13. Conventional spraying techniques may be used for this purpose. Such spraying is preferably performed at 80° C. and does not require a subsequent solvent evaporation step. Micro-spraying may be used to create solid polymer electrolyte patches on the support, such patches, if desired, being far smaller than those capable of being produced by masked coating techniques.

Still another technique for incorporating the solid polymer electrolyte 15 into support 13 involves a membrane extrusion technique. Such a technique comprises providing a solid polymer electrolyte in the form of a thin membrane, stacking the thin precursor membrane on the top and/or bottom surfaces of support 13, and then pressing the stack together at an elevated temperature, preferably above the melting point or glass transition temperature of the membrane, so that the membrane melts and is forced into pores 21. In those instances in which the membrane does not melt upon heating, but rather, degrades upon heating, a membrane precursor may be heated and forced into the pores and thereafter may be chemically converted to the corresponding solid ionomer. For example, if one wished to fill pores 21 with a PFSA (which does not melt, but instead, degrades upon heating), one could use a PFSA precursor in which the acid groups are replaced with sulfonyl fluoride groups. In such a case, once the sulfonyl fluoride precursor has melted and has been forced into pores 21, a base may be added to the PFSA precursor to convert the PFSA precursor into PFSA by base hydrolysis. Where support 13 is made of alumina or another ceramic material that degrades in the presence of a strong base (i.e., a base that donates an $OH^-$ group), a Lewis base (i.e., a base that accepts an $H^+$), such as imidazole, is preferably used to convert the sulfonyl fluoride PFSA precursor into PFSA.

Still yet another technique for incorporating the solid polymer electrolyte 15 into support 13 involves filling pores 21 with a corresponding monomer and then polymerizing the monomer in situ to form the desired solid ionomer. Such polymerization may be effected with the use of an initiator (e.g., vinyl) mixed in with the monomer or by radiation (e.g., UV radiation).

Figure 6:
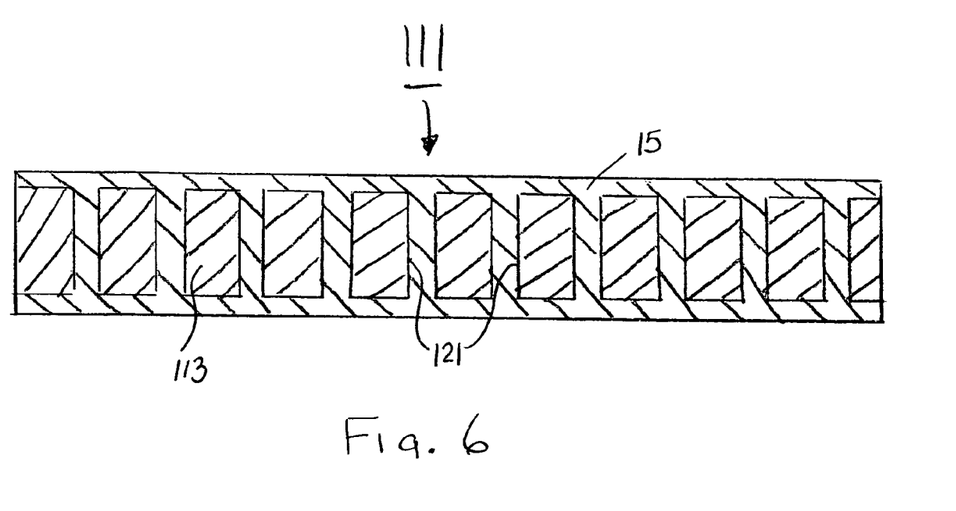
FIG. 6 is a schematic section view of a third embodiment of a solid polymer electrolyte composite membrane constructed according to the teachings of the present invention.

Referring now to FIG. 6, there is shown a schematic section view of a third embodiment of a solid polymer electrolyte composite membrane constructed according to the teachings of the present invention, said solid polymer electrolyte composite membrane being represented generally by reference numeral 111.

Figure 7:
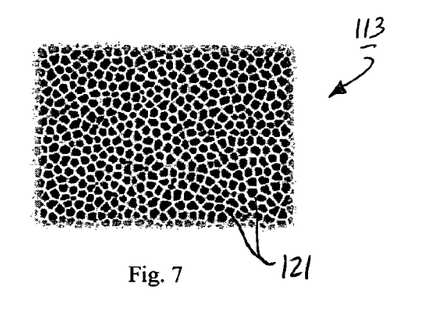
FIG. 7 is an image, taken from the top, of the non-electrically-conductive support of FIG. 6.

Composite membrane 111 is similar in many respects to membrane 11, the principle difference between the two membranes being that, whereas membrane 11 includes a ceramic support 13 whose pores 21 are formed by laser micromachining, membrane 111 includes a ceramic support 113 whose pores 121 are formed by the controlled electrochemical oxidation (i.e., pitting) of a sheet of the base metal (e.g., aluminum, titanium, etc.). A top view of support 113 is shown in FIG. 7. As can be seen, support 113 has a honeycomb-like arrangement of pores 121. WHATMAN ANODISC membrane filter, which is commercially available from Whatman International (United Kingdom) and is marketed for filtration purposes, is made of alumina and may be used support 113.

Pores 121 made by pitting a sheet of the base metal may have a diameter as small as about 0.01 μm. However, it should be noted that, where the diameter of pores 121 is less than about 0.1 μm, pores 121 cannot easily be filled using a solution or dispersion of the solid ionomer. Consequently, preferred techniques for filling such small pores include the hot-extrusion and in-situ polymerization techniques described above.

The total thickness of membrane 11 or 111 is preferably about 5 to 300 µm, more preferably 10 to 75 µm, with the thickness of the membrane being governed by application requirements. Generally, a water electrolyzer requires a thicker membrane due to its high differential pressure while an ultra-thin membrane is suitable for super capacitors since no dynamic pressure is involved for their operation.

Membrane and electrode assemblies (MEAs) comprising the composite membrane of the present invention can be fabricated by pressing a precast Pt-supported on carbon/ionomer ink onto each side of the composite membrane. The foregoing method is typically referred to as the decal transfer method.

One of the advantages of the composite membrane of the present invention is that catalyst ink can be directly coated or sprayed onto the top and bottom surfaces of the membrane. This direct coating of the catalyst ink is not practical for conventional ionomer membranes since such membranes change dimension when contacted with the ink. Since the composite membrane of the present invention has excellent dimensional stability when contacted with swelling agents, such as water or alcohols, the catalyst ink can be directly applied to the membrane.

Another approach that may be used to fabricate an MEA using the composite membrane of the present invention involves a technique called "catalyst on diffusion media." The diffusion medium of this technique is a porous electrically-conductive material, which is typically in the form of a thin sheet. Optionally, a microporous layer prepared from carbon black and a polymer binder may be applied to the diffusion medium. The catalyst is then sprayed onto the diffusion medium to form a diffusion electrode. A catalyst-loaded diffusion electrode is then pressed onto each side of the composite membrane to form a full MEA.

The following examples are provided for illustrative purposes only and are in no way intended to limit the scope of the present invention:

Example 1

A plurality of pores were formed in a piece of 25 µm thick silica film using an excimer laser and near-field imaging. The diameter of each pore was 30 µm, and the distance between the centers of the pores was 60 µm. NAFION® PFSA solution, with an equivalent weight of 1100, was coated onto the porous film, and the product was then heated to dry off the solvent from the coated PFSA solution and to cure the PFSA polymer. The resultant composite membrane had a thickness of approximately 32 µm. The wet through-plane conductivity of the membrane was 0.05 S/cm, as compared to 0.10 S/cm for the neat ionomer.

Example 2

A 25 µm NAFION® precursor membrane in the sulfonyl fluoride form was pressed into a 60 µm WHATMAN ANODISC filter having a 1.0 µm pore size. Such pressing was effected at 350° C. at 300 psi for 1 hour. Conversion of the sulfonyl fluoride form of the membrane was then effected by hydrolyzing overnight with imidazole at 60° C. The resulting wet room temperature through-plane-conductivity of the membrane was 0.04 S/cm, as compared to 0.10 S/cm for the neat ionomer.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A solid polymer electrolyte composite membrane, said solid polymer electrolyte composite membrane comprising:
    (a) a ceramic support, said ceramic support having opposing top and bottom surfaces and a plurality of pores extending from said top surface to said bottom surface;
    (b) a first solid polymer electrolyte, said first solid polymer electrolyte completely filling all of said pores and covering said top and bottom surfaces of said ceramic support; and
    (c) a second solid polymer electrolyte positioned at least one of over the top and under the bottom of said first solid polymer electrolyte, said second solid polymer electrolyte differing from said first solid polymer electrolyte.

2. The solid polymer electrolyte composite membrane as claimed in claim 1 wherein each of said plurality of pores extends in a straight line perpendicularly from said top surface to said bottom surface.

3. The solid polymer electrolyte composite membrane as claimed in claim 1 wherein said plurality of pores are arranged in a non-random pattern.

4. The solid polymer electrolyte composite membrane as claimed in claim 3 wherein said plurality of pores are arranged in a hexagonal pattern.

5. The solid polymer electrolyte composite membrane as claimed in claim 1 wherein said pores are unevenly distributed throughout said ceramic support.

6. The solid polymer electrolyte composite membrane as claimed in claim 5 wherein said ceramic support has a periphery and wherein said pores are positioned in a greater concentration distal to said periphery than proximate to said periphery.

7. The solid polymer electrolyte composite membrane as claimed in claim 1 wherein said pores are arranged in a honeycomb pattern.

8. The solid polymer electrolyte composite membrane as claimed in claim 1 wherein said pores are cylindrical in shape.

9. The solid polymer electrolyte composite membrane as claimed in claim 1 wherein said pores have a diameter of about 0.01 to 200 microns.

10. The solid polymer electrolyte composite membrane as claimed in claim 9 wherein said pores have a diameter of about 1 to 200 microns.

11. The solid polymer electrolyte composite membrane as claimed in claim 9 wherein said pores have a diameter of about 0.01 to 100 microns.

12. The solid polymer electrolyte composite membrane as claimed in claim 1 wherein said pores constitute about 20% to 95% of said ceramic support.

13. The solid polymer electrolyte composite membrane as claimed in claim 12 wherein said pores constitute about 40% to 70% of said ceramic support.

14. The solid polymer electrolyte composite membrane as claimed in claim 1 wherein said ceramic support comprises a material selected from the group consisting of silica, quartz, glass, boron carbonate, silicon carbide, alumina, titania, silica tungstate, sintered valve metal oxides and non-conductive diamond or diamond-like coatings.

15. The solid polymer electrolyte composite membrane as claimed in claim 14 wherein said ceramic support comprises a ceramic selected from the group consisting of silica, alumina and silicon carbide.

16. The solid polymer electrolyte composite membrane as claimed in claim 15 wherein said ceramic support is made of alumina.

17. The solid polymer electrolyte composite membrane as claimed in claim 1 wherein said ceramic support has a thickness of about 1 to 50 microns.

18. The solid polymer electrolyte composite membrane as claimed in claim 17 wherein said ceramic support has a thickness of about 7.5 to 15 microns.

19. The solid polymer electrolyte composite membrane as claimed in claim 1 wherein said first solid polymer electrolyte is selected from the group consisting of polymer compositions that contain metal salts, polymeric gels that contain electrolyte and ion exchange resins.

20. The solid polymer electrolyte composite membrane as claimed in claim 19 wherein said first solid polymer electrolyte is an ion exchange resin.

21. The solid polymer electrolyte composite membrane as claimed in claim 20 wherein said first solid polymer electrolyte is perfluorosulfonic acid (PFSA) polymer.

22. The solid polymer electrolyte composite membrane as claimed in claim 21 wherein said PFSA polymer has an equivalent weight of about 200 to 2000.

23. The solid polymer electrolyte composite membrane as claimed in claim 22 wherein said PFSA polymer has an equivalent weight of about 500 to 1200.

24. The solid polymer electrolyte composite membrane as claimed in claim 1 wherein said solid polymer electrolyte composite membrane has a thickness of about 5 to 300 microns.

25. The solid polymer electrolyte composite membrane as claimed in claim 24 wherein said solid polymer electrolyte composite membrane has a thickness of about 7.5 to 200 microns.

26. The solid polymer electrolyte composite membrane as claimed in claim 1 wherein said solid polymer electrolyte composite membrane has an ionic conductivity of 0.001 S/cm to 0.7 S/cm at room temperature with a relative humidity of 100%.

\* \* \* \* \*